(12) United States Patent
Recanati et al.

(10) Patent No.: US 11,931,211 B2
(45) Date of Patent: Mar. 19, 2024

(54) INTEGRATED INTRACORPOREAL LAPAROSCOPE CLEANER

(71) Applicants: Maurice Andre Recanati, New York, NY (US); Katherine Kramer, Philadelphia, PA (US); Hanna G. Ozbeki, Novi, MI (US); Rebeca Kelly, Clawson, MI (US); Apoorv Talekar, Detroit, MI (US); Satinder Kaur, Troy, MI (US); Michael Croft, Shelby Township, MI (US); Wesley Kuuttila, Farmington Hills, MI (US); Theresa Bonucci, Rochester Hills, MI (US); Charles Vanerian, Plymouth, MI (US)

(72) Inventors: Maurice Andre Recanati, New York, NY (US); Katherine Kramer, Philadelphia, PA (US); Hanna G. Ozbeki, Novi, MI (US); Rebeca Kelly, Clawson, MI (US); Apoorv Talekar, Detroit, MI (US); Satinder Kaur, Troy, MI (US); Michael Croft, Shelby Township, MI (US); Wesley Kuuttila, Farmington Hills, MI (US); Theresa Bonucci, Rochester Hills, MI (US); Charles Vanerian, Plymouth, MI (US)

( * ) Notice: Subject to any disclaimer, the term of this patent is extended or adjusted under 35 U.S.C. 154(b) by 519 days.

(21) Appl. No.: 17/193,103

(22) Filed: Mar. 5, 2021

(65) Prior Publication Data

US 2021/0275277 A1    Sep. 9, 2021

Related U.S. Application Data

(60) Provisional application No. 62/985,466, filed on Mar. 5, 2020.

(51) Int. Cl.
*A61B 90/70*    (2016.01)
*A61B 17/34*    (2006.01)
*A61B 17/00*    (2006.01)

(52) U.S. Cl.
CPC .......... *A61B 90/70* (2016.02); *A61B 17/3421* (2013.01); *A61B 17/3474* (2013.01); *A61B 17/3498* (2013.01); *A61B 2017/00973* (2013.01)

(58) Field of Classification Search
CPC ........ A61B 90/70; A61B 17/3421; A61B 1/12
See application file for complete search history.

(56) References Cited

U.S. PATENT DOCUMENTS 8,047,215 B1    11/2011    Sasaki
8,752,230 B2 *  6/2014    Brand ................ A61B 1/00131
                                                        15/210.1

(Continued)

FOREIGN PATENT DOCUMENTS

EP    0549739 A1    7/1993

*Primary Examiner* — Michael D Jennings
(74) *Attorney, Agent, or Firm* — Jacob M. Ward; Ward law Office LLC

(57) ABSTRACT

A medical device for cleaning a laparoscope can include a service box with a pump and a gas valve. Each of the pump and the gas valve can be in communication with an exit valve. The pump can be configured to draw fluid into the service box, along a fluid feed line, and out of the exit valve. The gas valve can be configured to selectively permit gas into the service box, along the fluid feed line, and out of the exit valve. The medical device can include a trocar that can be in communication with the exit valve via a flexible tubing. The trocar can include a hub and a cannula. The hub can be configured to receive and direct the laparoscope through the cannula. The cannula can be configured to receive fluid and gas from the exit valve and direct the fluid and gas to the open end.

20 Claims, 4 Drawing Sheets

(56) References Cited

U.S. PATENT DOCUMENTS

| | | |
|---|---|---|
| 9,545,194 B2 | 1/2017 | Nguyen |
| 2009/0240111 A1 | 9/2009 | Kessler et al. |
| 2018/0344427 A1* | 12/2018 | Rosenbaum ........... A61B 90/70 |
| 2019/0059713 A1* | 2/2019 | Allen ...................... B08B 1/001 |
| 2019/0231183 A1* | 8/2019 | Syed Ahmed ......... A61B 1/126 |

* cited by examiner

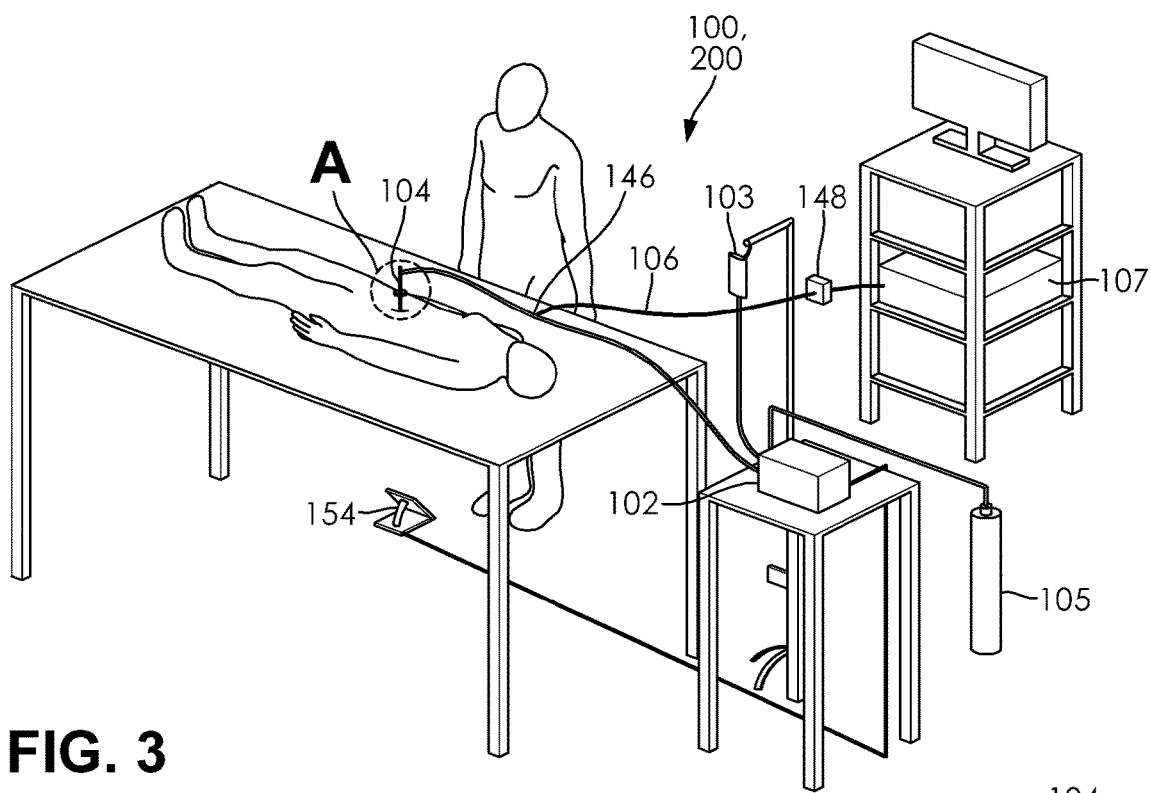
FIG. 3
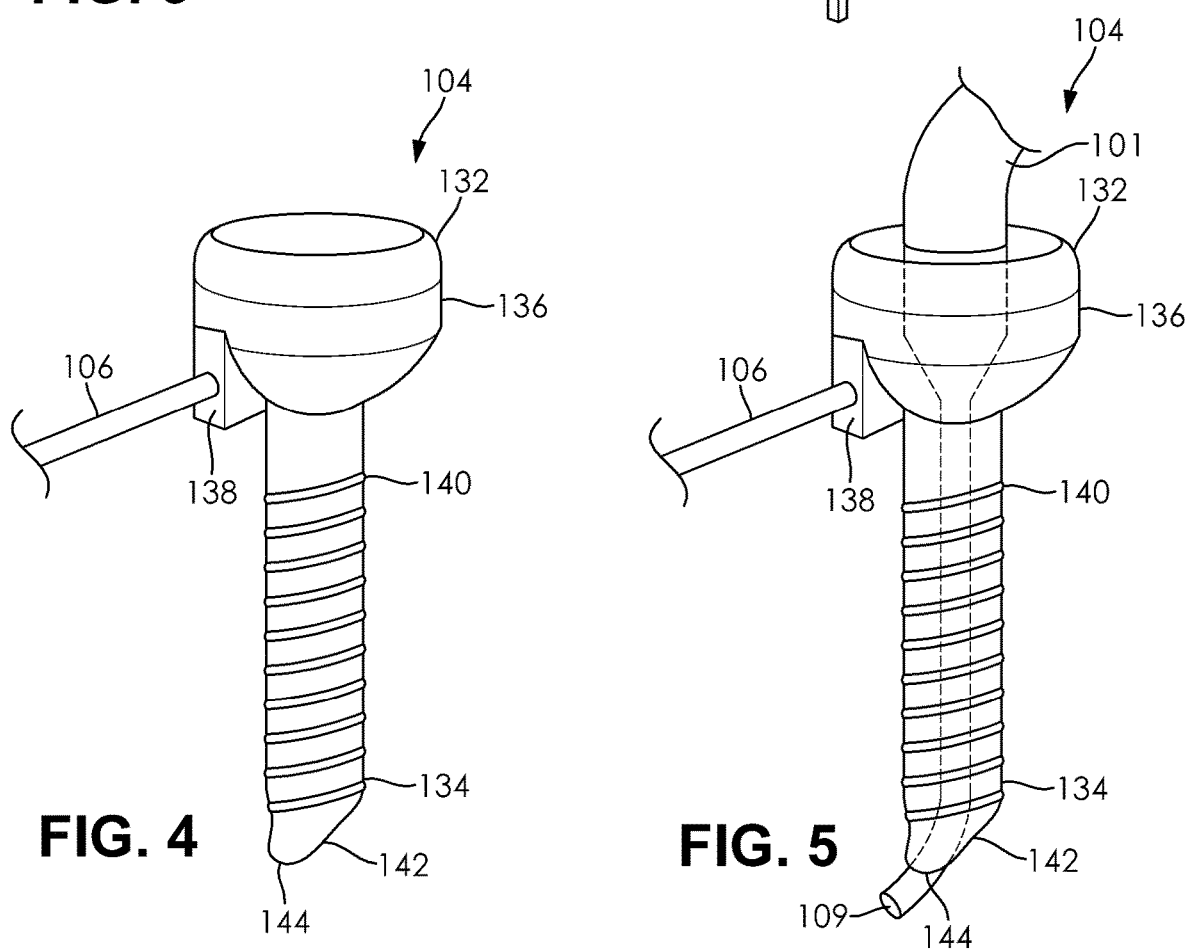
FIG. 4     FIG. 5

INTEGRATED INTRACORPOREAL LAPAROSCOPE CLEANER

CROSS-REFERENCE TO RELATED APPLICATIONS

This application claims the benefit of U.S. Provisional Application Ser. No. 62/985,466 filed on Mar. 5, 2020. The entire disclosure of the above application is incorporated herein by reference.

FIELD

The present disclosure relates to a medical device which can be used during minimally invasive surgery to maintain visualization of the surgical field and, more particularly, to a medical device which permits a laparoscope to be cleaned intracorporeally.

INTRODUCTION

This section provides background information related to the present disclosure which is not necessarily prior art.

Laparoscopic surgery is a minimally invasive technique for performing surgical procedures without resorting to more invasive surgical procedures. This approach is increasingly used by many surgical specialties as it affords greater safety, superior visualization, faster patient recovery and minimizes surgical blood loss. The technique involves creating small incisions on the abdomen through which trocar sleeves are introduced into an abdominal cavity that is distended with carbon dioxide gas to create a pneumoperitoneum.

A laparoscopic camera, as well as instruments, can be placed through the trocar sleeves allowing an operator (e.g., a surgeon) to operate under direct visualization. Frequently the laparoscope fogs up or comes into contact with blood or other fluids which blocks the lens and obscures the view. Traditionally, the laparoscope is removed from the patient and cleaned using cotton pads and lens defogger solutions before being re-introduced into the body. During this time, the operator is blind as to what is happening in the surgical field inside the patient. Loss of visualization is undesirable and can present issues when surgical instruments are grasping tissues or when active bleeding is occurring in the surgical field. To continue the cleaning process, the operator must also wipe down the trocar port site, which is also likely stained from the fluid or debris that has been tracked through by the scope as it was removed. This requires additional time, and depending on the amount of staining, the trocar may need to be at least partially disassembled, so that it can be more thoroughly cleaned.

After cleaning, the operator reinserts the scope through the clean trocar. However, the lens can quickly become stained again, obstructing the operator's vision and necessitating another cleaning. Each time the operator removes the lens for cleaning and subsequently reinserts, the operator must also reorient to the patient's anatomy. It also may be necessary to adjust anatomy in the surgical field.

There is a continuing need for a medical device configured to clean a laparoscope without removing it from the surgical site and having to stop the surgery to perform such action. Desirably, the medical device is a surgical instrument that facilitates laparoscopic surgery by allowing the laparoscope to be cleaned without removing it from the patient and prevents a dangerous situation in which the surgical field is not visualized.

SUMMARY

In concordance with the instant disclosure, a medical device configured to clean a laparoscope without removing it from the surgical site and having to stop the surgery to perform such action, and which is a surgical instrument that facilitates laparoscopic surgery by allowing the laparoscope to be cleaned without removing it from the patient and prevents a dangerous situation in which the surgical field is not visualized, is surprisingly discovered.

The present technology provides a medical device that allows an operator to clean a laparoscope without having to remove the laparoscope from a patient's abdomen. The medical device can maximize safety as it prevents moments in which the operator cannot visualize the surgical field. The medical device can be safer than conventional tools as it has no parts which can separate during surgery. The medical device can further keep the laparoscope lens dry after cleaning and prevent condensation and fog from forming thereon through use of a warm physiological saline solution as well as the same gas used to establish and maintain a pneumoperitoneum during the laparoscopic procedure.

Objects and advantages of the present technology include the following non-limiting examples:
  i. To provide a device capable of cleaning the laparoscope without removing it from the abdomen.
  ii. To provide a device that has no moving parts and no small loose parts that can separate inside a patient.
  iii. To provide a device that uses physiological saline under pressure as a means of cleaning the laparoscope lens.
  iv. To provide a device that uses warm saline as a means of rapidly bringing the laparoscopic lens to body temperature and prevent fogging and condensation.
  v. To provide a device that uses a puff of carbon dioxide to dry the lens assembly.
  vi. To provide a device that can, at the push of a button, sequence a bolus of saline and the puff of carbon dioxide with minimal intervention by the operator.
  vii. To provide a device that is easy to assemble prior to laparoscopic surgical cases.
  viii. To provide a device that is safe to use and has no sharp angles.
  ix. To provide a disposable device.
  x. To provide a device that can interface with existing carbon dioxide insufflators and regulators commonly used in the operating room as well as normal saline containers, such as IV bags, which are found in the medical setting In certain embodiments, a medical device for intracorporeally cleaning a laparoscope can include a service box. The service box can include a pump and a gas valve. Each of the pump and the gas valve can be in communication with an exit valve via a fluid feed line. The pump can be configured to draw fluid into the service box, along the fluid feed line, and out of the exit valve. The gas valve can be configured to selectively permit a transfer of gas into the service box, along the fluid feed line, and out of the exit valve. The medical device can include a trocar that can be in communication with the exit valve via a flexible tubing. The trocar can include a hub and a cannula. The cannula can have an open end. The hub can be configured to receive the laparoscope and direct the laparoscope through the open end of the cannula. The cannula can be configured to receive fluid and gas from the exit valve and direct the fluid and gas to the open end, thereby cleaning the lens of the laparoscope.

In certain other embodiments, a method of performing a laparoscopic procedure is provided where the method provides a laparoscope and a medical device including a service. The service box can include a pump and a gas valve. Each of the pump and the gas valve can be in communication with an exit valve via a fluid feed line. The pump can be configured to draw fluid into the service box, along the fluid feed line, and out of the exit valve. The gas valve can be configured to draw gas into the service box, along the fluid feed line, and out of the exit valve. The medical device can include a trocar that can be in communication with the exit valve via a flexible tubing. The trocar can include a hub and a cannula. The cannula can have an open end. The hub can be configured to receive the laparoscope and direct the laparoscope through the open end of the cannula. The cannula can be configured to receive fluid and gas from the exit valve and direct the fluid and gas to the open end. The method can include a step of performing the laparoscopic procedure, which can include cleaning the laparoscope with the fluid and the gas from the medical device. In this way, the present technology can clean the laparoscope and restore full visualization for the operator without having to remove the laparoscope from the surgical field, optimizing the surgical procedure and overall efficiency.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3 is a top perspective view of the medical device of FIG. 1, further depicted in use during a laparoscopic procedure;

FIG. 4 is an enlarged view of a trocar of the medical device taken at callout A in FIG. 4;

FIG. 5 is an enlarged view of the trocar, taken at callout A in FIG. 4, further depicting the laparoscope inserted into the trocar;

DETAILED DESCRIPTION

Figure 1:
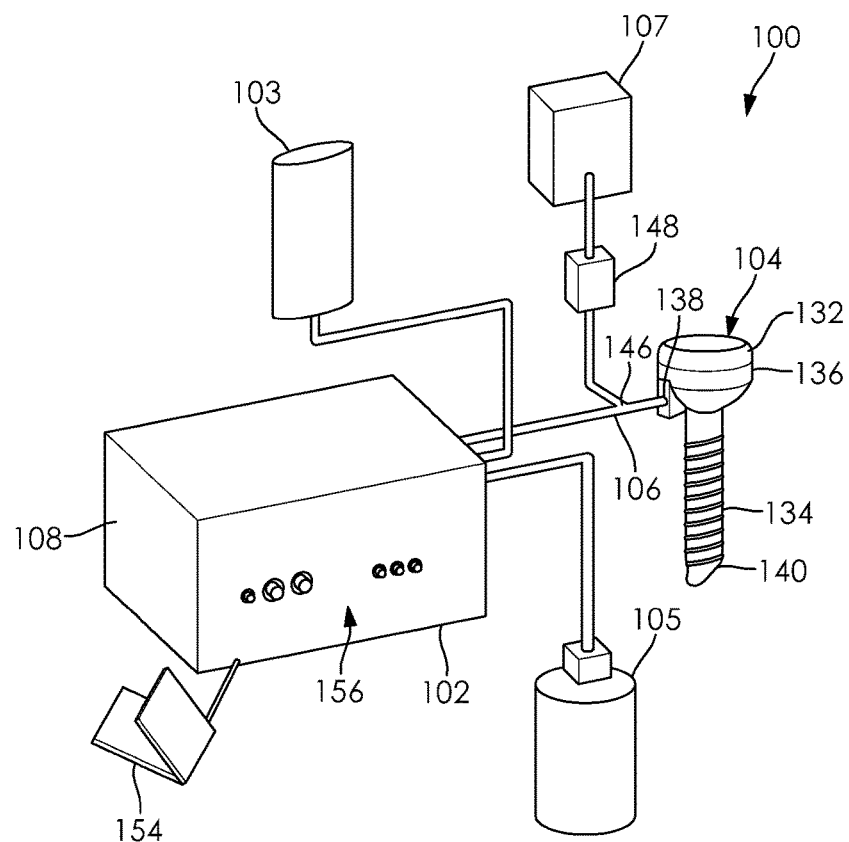
FIG. 1 is a top perspective view of a medical device, which permits a laparoscope to be cleaned intracorporeally.

The following description of technology is merely exemplary in nature of the subject matter, manufacture and use of one or more inventions, and is not intended to limit the scope, application, or uses of any specific invention claimed in this application or in such other applications as can be filed claiming priority to this application, or patents issuing therefrom. Regarding methods disclosed, the order of the steps presented is exemplary in nature, and thus, the order of the steps can be different in various embodiments, including where certain steps can be simultaneously performed, unless expressly stated otherwise. "A" and "an" as used herein indicate "at least one" of the item is present; a plurality of such items can be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that can arise from ordinary methods of measuring or using such parameters.

Although the open-ended term "comprising," as a synonym of non-restrictive terms such as including, containing, or having, is used herein to describe and claim embodiments of the present technology, embodiments can alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that can be recited in the art, even though element D is not explicitly described as being excluded herein.

When an element or layer is referred to as being "on," "engaged to," "connected to," or "coupled to" another element or layer, it can be directly on, engaged, connected, or coupled to the other element or layer, or intervening elements or layers can be present. In contrast, when an element is referred to as being "directly on," "directly engaged to," "directly connected to" or "directly coupled to" another element or layer, there can be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. can be used herein to describe various elements, components, regions, layers and/or sections, these elements, components, regions, layers and/or sections should not be limited by these terms. These terms can be only used to distinguish one element, component, region, layer, or section from another region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings of the example embodiments.

Spatially relative terms, such as "inner," "outer," "beneath," "below," "lower," "above," "upper," and the like, can be used herein for ease of description to describe one element or feature's relationship to another element(s) or feature(s) as illustrated in the figures. Spatially relative terms can be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

As shown in FIGS. 1-7, an embodiment of a medical device 100, which permits a laparoscope 101 to be cleaned intracorporeally, is shown. The medical device 100 can include a service box 102 and trocar 104. The service box 102 and trocar 104 can be connected by a flexible tubing 106.

The service box 102 can include a plurality of side walls 108. The side walls 108 can define an interior 110 of the service box 102. The side walls 108 can include a plurality of ports 112 formed therethrough. The ports 112 can be configured to allow various forms of tubing or wiring to pass into the interior 110 of the service box 102, as described in greater detail hereinbelow. It should be appreciated that each of the ports 112 of the service box 102 can include a Luer lock. Each of the Luer locks can be a threaded Luer taper lock. It should be appreciated that the Luer lock can militate against leaks at the ports 112, in operation. A skilled artisan can select other fluid-tight couplings, including other suitable Luer locks, as desired, to militate against leaks from the service box 102.

Figure 2:
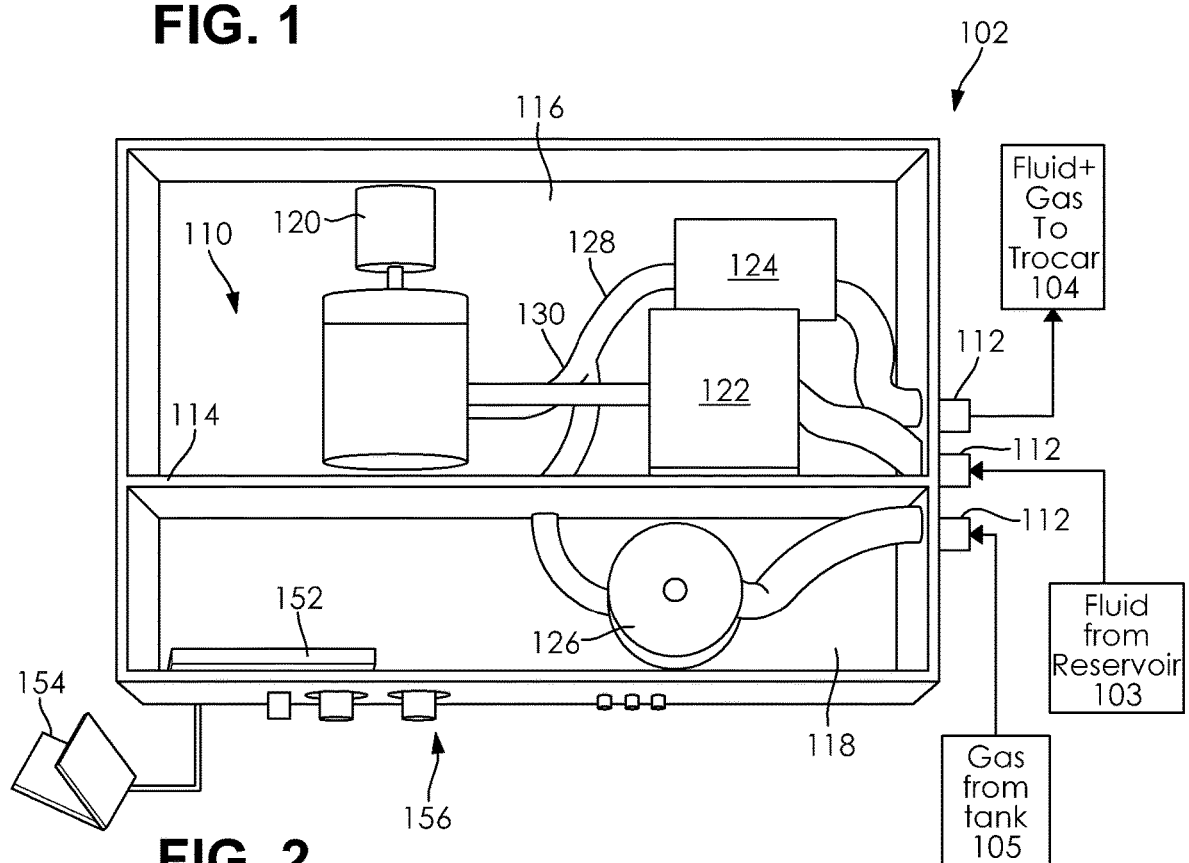
FIG. 2 is a top plan view of an interior of a service box of the medical device shown in FIG. 1.

With reference to FIG. 2, the interior 110 of the service box 102 can include a divider wall 114. The divider wall 114 can define two discrete compartments within the service box 102, namely, an operational compartment 116 and an electrical compartment 118. The divider wall 114 can be configured to isolate electrical components of the electrical compartment 118 of the service box 102 from operational components of the service box 102. The operational components can contain fluids, as described in greater detail hereinbelow. Advantageously, the divider wall 114 can militate against damage to the electrical components if the fluids of the operational components were to undesirably leak, in operation.

The service box 102 can include a pump 120 disposed in the operational compartment 116 therein. The pump 120 can be in fluid communication with a reservoir 103. As a non-limiting example, the reservoir can be an IV bag. In particular, an IV tube can be fluidly coupled to or disposed through one of the ports 112 of the service box 102 and fluidly connected to the pump 120. In certain embodiments, the pump 120 can be a peristaltic pump. In certain embodiments, the pump 120 can be configured to pump saline from the reservoir 103 to the service box 102, as one non-limiting example. A skilled artisan can employ other suitable pumps 120, as desired.

The pump 120 can be in fluid communication with a fluid heater 122, which can also be disposed in the operational compartment 116 of the service box 102. The fluid heater 122 can be disposed between the reservoir 103 and the pump 120. As the pump 120 draws fluids from the reservoir 103, the fluids can be warmed by the fluid heater 122. The fluid heater 122 can be configured to heat the fluid entering the pump 120 to a predetermined temperature. In certain examples, the predetermined temperature can be about 37° C. Other suitable temperatures can be selected by a skilled artisan, as desired.

With continued reference to FIG. 2, the service box 102 can include an exit valve 124. The exit valve 124 can be in fluid communication with the pump 120 and a gas valve 126. The exit valve 124 can be disposed in the operational compartment 116 of the service box 102. The exit valve 124 can be a one-way valve. The exit valve 124 can be configured to militate an undesirable reflux of gas or fluids into the service box 102, in operation.

The gas valve 126 can be in fluid communication with a gas tank 105. The gas tank 105 can be coupled or connected to the gas valve 126 via tubing through one of the ports 112 of the service box 102. The gas valve 126 can be actuated by a solenoid (not shown). The gas valve 126 can receive gas from the gas tank 105 and can selectively permit a controlled amount of gas to pass through to the exit valve 124, in operation. In some example embodiments, the gas tank 105 can include carbon dioxide.

The pump 120 and the gas valve 126 can be connected to the exit valve 124 via a fluid feed line 128. The fluid feed line 128 can have a first end that can be attached to the exit valve 124. The fluid feed line 128 can have a Y-shaped junction 130, which splits a second end of the fluid feed line 128. The Y-shaped junction 130 allows for a fluid connection with each of the pump 120 and the gas valve 126. Advantageously, the fluid feed line 128 allows for both liquid and gas to travel through the fluid feed line 128, in operation, such that it is necessary to only provide one exit valve 124 within the service box 102 to militate against reflux.

With reference to FIGS. 4-5, the trocar 104 can include a hub 132 and a cannula 134. The cannula 134 can be configured to traverse skin of a patient skin to and enter a peritoneal cavity of the patient, for example, as shown in FIG. 3. The trocar 104 can include a check valve 136 disposed between the hub 132 and the cannula 134. The check valve 136 can be fabricated of a rubber or rubberized material, as non-limiting examples. The check valve 136 can form a seal with the body of the patient, while allowing the laparoscope 101 to pass into the cannula 134. Advantageously, the check valve 136 can allow for maintaining pneumoperitoneum conditions while the laparoscope 101 is utilized.

The trocar 104 can include a side port 138. The side port 138 can be disposed below the check valve 136. The side port 138 can include a Luer lock. The side port 138 can receive the flexible tubing 106, which fluidly couples the trocar 104 to the service box 102. In particular, the flexible tubing 106 can place the side trocar 104 in fluid communication with the exit valve 124 such that fluids including liquid (e.g., warmed saline) and gas (e.g., $CO_2$) from the exit valve 124 can flow through the flexible tubing 106 through the side port 138 and into the cannula 134.

With reference to FIG. 4-5, the cannula can have a groove 140 formed on an interior surface thereof. The groove 140 can have a corkscrew shape. The corkscrew shape can wind along a length of the cannula 134. Advantageously, the groove 140 can direct fluids and gases from the side port 138 along the length of the cannula 134 in a manner that generates a vortex flow of the fluid.

The cannula 134 can have an open beveled end 142 opposite of the hub 132. The beveled end 142 can be configured to be inserted into the patient. In operation, when the laparoscope 101 is disposed in the trocar 104, the laparoscope 101 can pass through the open beveled end 142 of the cannula 134 and into the patient. The cannula can have a vane 144 formed on the interior surface adjacent the beveled end 142. The vane 144 can be configured to direct fluid (e.g., charges of liquid and gas) within the cannula 134 to a lens 109 of the laparoscope 101, thus, allowing the lens 109 of the laparoscope 101 to be cleaned of debris via the fluid flow from the vane 144. Advantageously, the lens 109 of the laparoscope 101 can be cleaned via the flow of liquid and gas from the service box 102, to the trocar 104, without removing the laparoscope 101 from the patient. In particular, the liquid can remove debris from the lens 109 and the gas can dry the excess fluid from the lens 109, thus allowing the lens 109 to be cleaned and dried to militate against the formation of fog on the lens 109, in operation.

With renewed reference to FIGS. 1 and 3, the flexible tubing 106, which connects the service box 102 to the trocar 104, can include a Y-shaped connector 146. The Y-shaped connector 146 can allow the flexible tubing 106 to also be connected to a laparoscopic insufflator 107, which can be found in an operating room. The laparoscopic insufflator 107 can allow carbon dioxide to flow into the patient and maintain the pneumoperitoneum during surgery. The flexible tubing 106 can include a valve 148 disposed between the trocar 104 and the laparoscopic insufflator 107. The valve 148 can militate against the laparoscopic insufflator 107 from ingesting fluid from the trocar 104, in operation.

The medical device 100 can include a control system 150. The control system 150 can include a circuit board 152. The circuit board 152 can be in communication with a power source. The circuit board 152 can be configured to actuate the pump 120 and the solenoid of the gas valve 126. The control system 150 can be actuated by a pedal 154. The pedal 154 can allow an operator to actuate the medical device 100 by the operator's a foot, allowing for continued control of any surgical tools in the operator's hands, in operation. The operator can depress the pedal 154, which can power the circuit board 152 to signal the pump 120 and the gas valve 126. The pump 120 can then pump a volume of fluid from the reservoir 103 and the gas valve 126 can allow a volume of gas into the service box 102. The control system 150 can include a control panel 156. The control panel 156 can include a plurality of knobs, which can adjust each of the volume of fluid and the volume of gas released by the medical device 100 when the pedal 154 is depressed by the operator. The control panel 156 can further include a power switch, which allows the medical device 100 to be powered on. The control panel 156 can include a panel of lights, which can display a power status or signal internal errors, such as low carbon dioxide pressure and undesirable fluid temperature.

Figure 6:
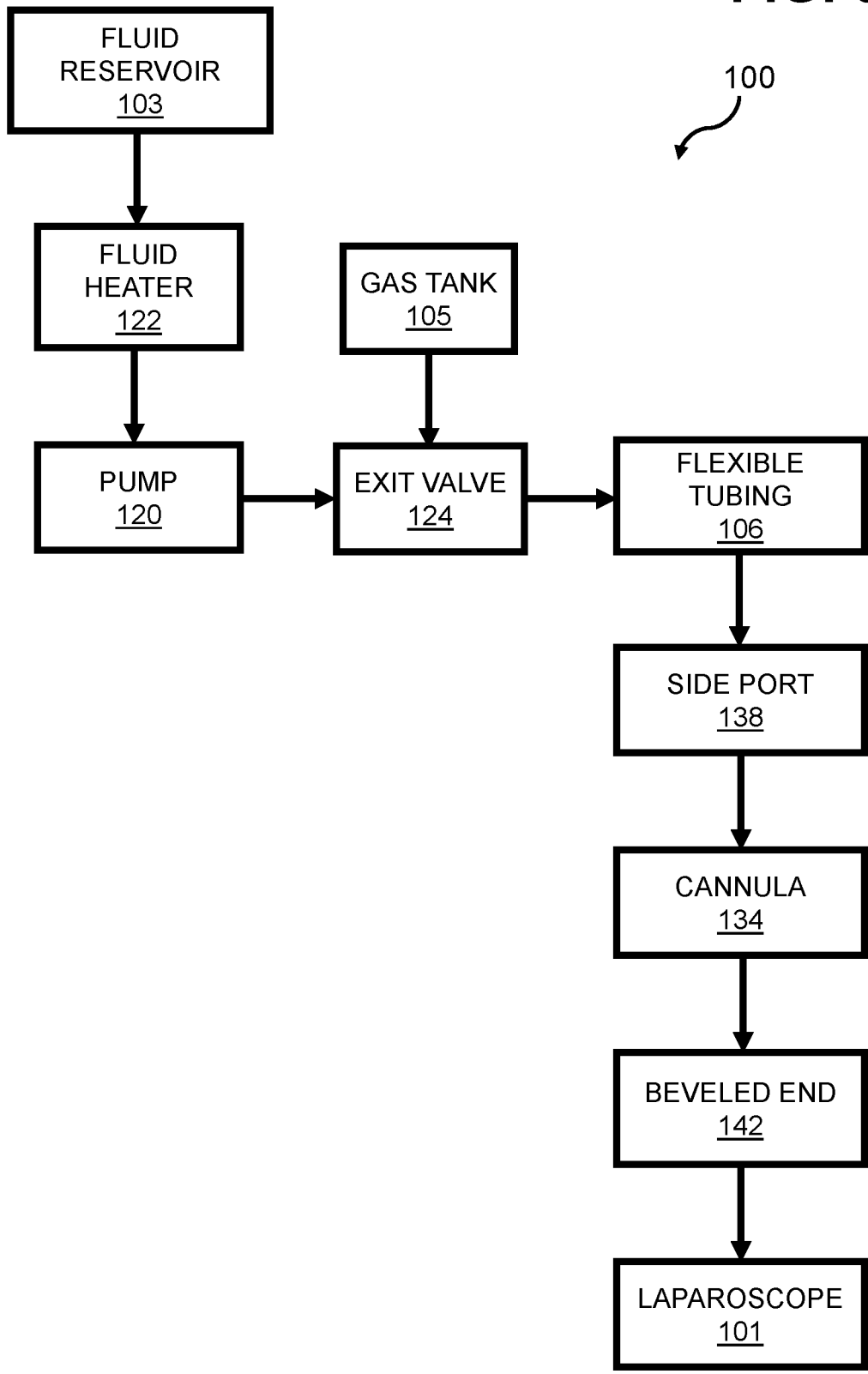
FIG. 6 is a flow chart illustrating a one-way fluid flow of the medical device shown in FIG. 1.

It should be appreciated that the medical device 100 of the present disclosure can allow for a one-way fluid flow of liquid and gas, in operation, for example, as illustrated in FIG. 6. In particular, when the pedal 154 is depressed, saline can flow from the reservoir 103 through the fluid heater 122 via the pump 120. Then, the saline can flow through the exit valve 124 via the fluid feed line 128. The volume of carbon dioxide can then be pumped by the gas valve 126 from the gas tank 105 into the fluid feed line 128 after the saline and through the exit valve 124. The saline and carbon dioxide can then flow out of the service box 102 via the flexible tubing 106 and into the side port 138 of the trocar 104. The saline and carbon dioxide can flow through the groove 140 of the cannula 134 to the beveled end 142 of the cannula. In particular, the fluid can encounter the groove 140, which can cause the vortex flow of the fluid. The vortex flow will drive a charge of the fluid to the beveled end 142. The fluid can then be directed by the vane 144 onto the lens 109 of the laparoscope 101 when the lens 109 is disposed adjacent to the vane 144, for example, as shown in FIG. 5. It should be appreciated that the groove 140 can allow the fluid to flow smoothly through the cannula 134, and the vane can direct the flow of the fluid to the lens 109, thereby allowing the lens 109 to be cleaned by the charge of fluid.

Figure 7:
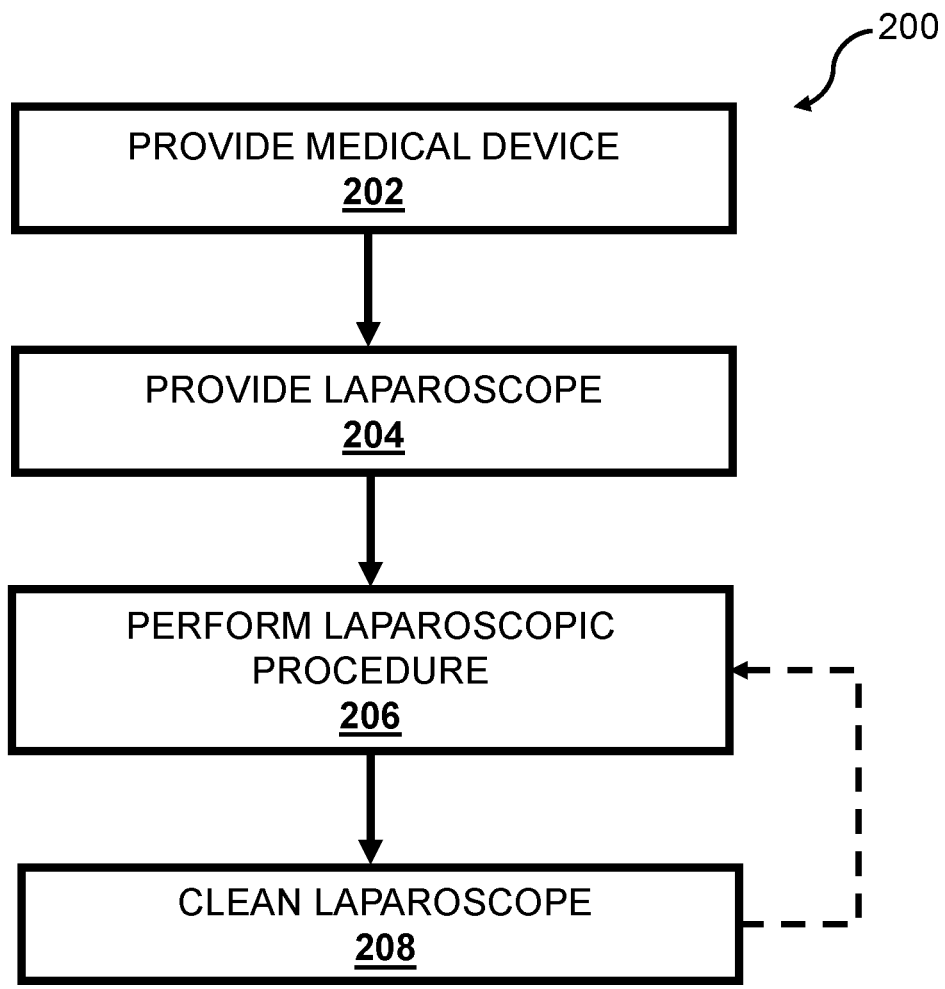
FIG. 7 is a flow chart illustrating a method according to a further embodiment of the present disclosure.

With reference to FIG. 7, the present disclosure further contemplates a method of performing a laparoscopic procedure 200. The method 200 can include a first step 202 of providing the medical device 100, which can permit the laparoscope 101 to be cleaned intracorporeally, as described herein. The service box 102 can be powered on. The reservoir 103 with saline and the gas tank 105 with carbon dioxide can each be fluidly connected to ports 112 of the service box 102. A second step 204 of the method 200 can include providing the laparoscope 101 with the laparoscopic insufflator 107.

The method 200 can include a third step 206 of beginning the laparoscopic procedure. The third step can include inserting the trocar 104 into the patient. The laparoscope 101 can then be inserted through the hub 132 and through the cannula 134 of the trocar 104. The laparoscopic insufflator 107 can be used to create the necessary pneumoperitoneum.

A fourth step 208 in the method 200 can include cleaning the lens 109 of the laparoscope 101 with the medical device 100. In particular, the operator can press the pedal 154. The pedal 154 can power the circuit board 152, which can then signal the pump 120 and the gas valve 126. The service box 102 can then send saline and carbon dioxide to the trocar 104 through the one-way fluid flow described hereinabove and shown in FIG. 6. Accordingly, the fourth step 208 can be performed via the press of the pedal 154 without having to remove the laparoscope 101 from the patient, thus, maintaining sterility of the laparoscope 101. The fourth step 208 can be repeated, as necessary, throughout the duration of the procedure.

It should be appreciated that the medical device 100 of the present disclosure can allow an operator (e.g., a surgeon) to clean the laparoscope 101 without having to remove it from the abdomen of the patient, in operation. The medical device 100 can allow for a safer procedure as the medical device 100 can militate against moments in which the operator cannot visualize the surgical field. The medical device 100, disclosed herein, can be safer than conventional tools as the medical device 100 can have no separable parts. Additionally, the medical device 100 can be configured to use warm physiological saline solution as well as carbon dioxide, which is already used to establish and maintain the pneumoperitoneum necessary for the laparoscopic procedure. In other words, the medical device 100 can be operated without introducing undesirable materials into the patient, in order to clean the lens 109 of the laparoscope 101, in operation.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments can be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions, and methods can be made within the scope of the present technology, with substantially similar results.

What is claimed is:

1. A medical device for intracorporeally cleaning a laparoscope, comprising:
   a service box including a pump and a gas valve, each of the pump and the gas valve in fluid communication with an exit valve via a fluid feed line, the pump configured to transfer a liquid into the service box, through the fluid feed line, and out of the exit valve, the gas valve configured to selectively permit a transfer of gas into the service box, through the fluid feed line, and out of the exit valve; and
   a trocar in fluid communication with the exit valve via a flexible tubing, the trocar including a hub and a cannula having an open end, the hub configured to receive the laparoscope and direct the laparoscope through the open end of the cannula, the cannula configured to receive liquid and gas from the exit valve and direct the liquid and gas to the open end of the cannula, thereby cleaning the laparoscope when received by the hub.

2. The medical device of claim 1, further comprising a fluid heater configured to warm the fluid to a predetermined temperature.

3. The medical device of claim 1, wherein the service box includes a dividing wall, which defines an operational compartment and an electrical compartment.

4. The medical device of claim 3, wherein the pump is disposed in the operational compartment and the gas valve is disposed in the electrical compartment.

5. The medical device of claim 1, wherein the service box includes a plurality of fluid coupling ports.

6. The medical device of claim 5, wherein one of the ports is in fluid communication with the pump and is configured to be in fluid communication with a fluid reservoir.

7. The medical device of claim 5, wherein one of the ports is in fluid communication with the gas valve and is configured to be in fluid communication with a gas tank.

8. The medical device of claim 1, wherein the flexible tubing includes a Y-shaped connector.

9. The medical device of claim 8, wherein the Y-shaped connector is configured to place the trocar in simultaneous fluid communication with the service box and a laparoscopic insufflator.

10. The medical device of claim 1, wherein a groove is formed on an interior surface of the cannula of the trocar.

11. The medical device of claim 10, wherein the groove is a corkscrew shape.

12. The medical device of claim 10, wherein the groove extends along a length of the cannula.

13. The medical device of claim 1, wherein a vane is formed adjacent to the open end in the cannula.

14. The medical device of claim 1, further comprising a control system, the control system including a circuit board disposed in the service box.

15. The medical device of claim 14, wherein the circuit board is configured to signal the pump to direct a predetermined volume of fluid through the service box to the trocar, and to signal the gas valve to direct a predetermined volume of gas through the service box and to the trocar.

16. The medical device of claim 14, wherein the circuit board is configured to signal the gas valve to direct a predetermined volume of gas through the service box and to the trocar.

17. The medical device of claim 14, wherein the control system includes a pedal configured to actuate the circuit board.

18. The medical device of claim 1, further comprising:
   a fluid reservoir including saline in fluid communication with the service box; and
   a gas tank including carbon dioxide in fluid communication with the service box.

19. A method of performing a laparoscopic procedure, comprising:
   providing a laparoscope;
   providing a medical device including a service box with a pump and a gas valve, each of the pump and the gas valve in fluid communication with an exit valve via a fluid feed line, the pump configured to transfer a liquid into the service box, through the fluid feed line, and out of the exit valve, the gas valve configured to selectively permit a transfer of gas into the service box, through the fluid feed line, and out of the exit valve; and a trocar in fluid communication with the exit valve via a flexible tubing, the trocar including a hub and a cannula having an open end, the hub configured to receive the laparoscope and direct the laparoscope through the open end of the cannula, the cannula configured to receive liquid and gas from the exit valve and direct the liquid and gas to the open end of the cannula, thereby cleaning the laparoscope when received by the hub;
   performing the laparoscopic procedure; and
   cleaning the laparoscope with the liquid and the gas from the medical device.

20. The method of claim 19, wherein the step of cleaning the laparoscope is performed a plurality of times while performing the laparoscopic procedure.

* * * * *